United States Patent
Klaasen et al.

(10) Patent No.: US 8,628,766 B2
(45) Date of Patent: Jan. 14, 2014

(54) **VACCINE FOR PROTECTION AGAINST *STREPTOCOCCUS SUIS* BACTERIA OF VARIOUS SEROTYPES**

(75) Inventors: Henricus Leo Bernardus Maria Klaasen, Boxmeer (NL); Ruud Philip Antoon Maria Segers, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/258,589

(22) PCT Filed: Mar. 25, 2010

(86) PCT No.: PCT/EP2010/053887
§ 371 (c)(1),
(2), (4) Date: Sep. 22, 2011

(87) PCT Pub. No.: WO2010/108977
PCT Pub. Date: Sep. 30, 2010

(65) Prior Publication Data
US 2012/0021003 A1    Jan. 26, 2012

Related U.S. Application Data

(60) Provisional application No. 61/163,604, filed on Mar. 26, 2009.

(30) Foreign Application Priority Data

Mar. 26, 2009   (EP) ..................................... 09156277

(51) Int. Cl.
*A01N 63/00* (2006.01)
*A61K 39/09* (2006.01)
*A61K 39/02* (2006.01)
*A61K 39/00* (2006.01)

(52) U.S. Cl.
USPC .................. 424/93.44; 424/234.1; 424/184.1; 424/244.1; 424/825

(58) Field of Classification Search
None
See application file for complete search history.

(56) References Cited

U.S. PATENT DOCUMENTS

| 5,059,419 A | 10/1991 | Ruehling |
| 7,125,548 B2 | 10/2006 | Smith |
| 2011/0014237 A1* | 1/2011 | Segers et al. ............... 424/256.1 |

OTHER PUBLICATIONS

Willson et al. Annual Research Report—Praire Swine Centre Saskatoon 21: 27-28, 2003.*
Foster et al. Veterinary Research Communications 18: 155-163, 1994.*
Baums, C.G. et al. "Comparison of a *Streptococcus suis* Subunit Vaccine with a Bacterin in Immunization Experiments Including Homologous and Heterologous Challenges", Abstracts of the General Meeting of the American Society for Microbiology, vol. 108, p. 241, 108th General Meeting of the American Society for Microbiology, Boston, MA, Jun. 1-5, 2008 XP008109422.
Pejsak, Zygmunt et al. "Efficacy of Streptovac Vaccine for Controlling Streptococcosis", Medycyna Weterynaryjna, 64(1):113-116 (Jan. 2008) English Abstract.
Rasmussen, Soren R. et al. "16S rDNA Sequence Variations of Some *Streptococcus suis* Serotypes", International Journal of Systematic Bacteriology, 48:1063-1065 (1998).
Torremorrell, Montserrat et al. "Colonization of Suckling Pigs by *Streptococcus suis* with Particular Reference to Pathogenic Serotype 2 Strains", Canadian Journal of Veterinary Research, Canadian Veterinary Medical Association, Ottawa, CA 62:21-26 (Jan. 1998) XP000991159.
European Search Report corresponding to EP 09 15 6277, completed Aug. 10, 2009.
International Search Report corresponding to PCT/EP2010/053887, mailed May 20, 2010.
Pejsak et al., "Efficacy of Streptovac vaccine for controlling swine *Streptococcus*", Medycyna Weterynaryjna [Veterinary Medicine], 2008, 64(1): 113-116 (English Translation Attached).

* cited by examiner

*Primary Examiner* — S. Devi

(57) ABSTRACT

The present invention pertains to the use of *Streptococcus suis* antigens corresponding to *Streptococcus suis* bacteria of a predetermined serotype in the manufacture of a vaccine for administration to a sow or gilt, to protect a piglet through the intake of colostrum of the said sow or gilt, against a disorder arising from *Streptococcus suis* bacteria of a serotype other than the predetermined one. The invention also pertains to *Streptococcus suis* antigens for use in the manufacture of such a vaccine.

6 Claims, No Drawings

VACCINE FOR PROTECTION AGAINST *STREPTOCOCCUS SUIS* BACTERIA OF VARIOUS SEROTYPES

CROSS-REFERENCE TO RELATED APPLICATIONS

This application is a national stage entry under 35 U.S.C. §371 of PCT/EP2010/053887, filed on Mar. 25, 2010, which claims priority to U.S. Provisional Application No. 61/163,604, filed on Mar. 26, 2009, and EP Application No. 09156277.7, filed on Mar. 26, 2009. The content of PCT/EP2010/053887 is hereby incorporated by reference in its entirety.

The present invention pertains to a vaccine to protect piglets against *Streptococcus suis* bacteria of multiple serotypes, in particular provided by cross-protection against a heterologous strain.

*Streptococcus suis* is one of the principal etiologic agents of contagious bacterial disease in pigs. The pathogen can cause a variety of clinical syndromes including meningitis, arthritis, pericarditis, polyserositis, septicaemia, pneumonia and sudden death. *S. suis* is a gram-positive facultatively anaerobic coccus, originally defined as Lancefield groups R, S, R/S or T. Later, a new typing system based on the type-specific capsular polysaccharide antigens located in the cell wall was proposed. This led to a system comprising 35 serotypes (Rasmussen and Andresen, 1998, "16S rDNA sequence variations of some *Streptococcus suis* serotypes", Int. J. Syst. Bacteriol. 48, 1063-1065) of which serotypes 2, 1, 9, 7 and 1/2 are the most prevalent. Control of *S. suis* in pig herd is in general hampered by the lack of vaccines that provide protection against multiple serotypes, and the lack of diagnostic tests with high specificity and sensitivity. The limited availability of these tools is likely caused by the large number of existing serotypes, the variation in virulence among strains and the still scarce knowledge about the factors that contribute to virulence and protection.

Porcilis Strepsuis® is a registered vaccine (Intervet/Schering-Plough Animal Health) to protect swine against *Streptococcus suis* serotype 2. It also passively protects the offspring against serotype 2 via intake of the colostrum. However, it is not registered for protection against *Streptococcus suis* bacteria of other serotypes. Indeed, as is generally known for vaccines that actively protect against *Streptococcus suis*, cross protection against bacteria of other serotypes does not occur. This is confirmed i.a. in the PhD thesis of Hendrikus Jan Wisselink, titled "*Streptococcus suis* infection in pigs: Use of virulence-associated markers in diagnostics and vaccines", published 6 Dec. 2001. In the summary (page 129) it is stated that a "strategy to prevent disease caused by *S. suis* is by the use of vaccines. Killed whole-cell vaccines seem to induce significant protection against challenge with a strain of homologues serotype, but this protection is probably serotype-specific".

The above findings are in line with the findings by Smith (U.S. Pat. No. 7,125,548; published 24 Oct. 2006). She states that "antibodies are serotype-specific, and will often only confer protection against only one of the many serotypes known within a group of Streptococci. For example, current commercially available *S. suis* vaccines, which are generally based on whole-cell-bacterial preparations, or on capsule-enriched fractions of *S. suis*, confer only limited protection against heterologous strains." (column 4, lines 42-28 of the US patent). Recently a study was published (January 2008: Medycyna Weterynaryjna, Volume 64, issue 1, pages 113-116), describing protection against *S. suis* bacteria of serotypes 2 and 1/2. If there would be any expected level of cross-protection between different serotypes, it would be between these serotypes since they are immunologically very closely related. Still, both serotypes were comprised in the vaccine to obtain adequate protection. The UK based RUMA (Responsible Use of Medicines in agriculture Alliance) has published guidelines on the use of vaccines and vaccination in pig production in November 2006. With respect to disease caused by *S. suis*, these guidelines state (on page 19) that protection of the piglet can be achieved by vaccination of the sow, but that "protection against disease caused by other *Strep. suis* serotypes is unlikely to occur."

The disadvantage of hitherto known vaccines is that for protection against the serotypes that are most prevalent, i.e. serotypes 2 and 1, and to a lesser extent 9 and 7, all serotypes against which protection should be provided have to be in the vaccine. This is disadvantageous from a safety point of view (more bacteria present often leads to a higher LPS content of the vaccine), but also from an economical point of view: the presence of multiple types of bacteria in the vaccine implies a higher chance of vaccine batch failure and a higher risk of contamination. Therefore, the chance of a vaccine batch being found unfit for sales is increased. It is therefore an object of the present invention to overcome or at least mitigate the disadvantages of the present vaccines against *Streptococcus suis* and to arrive at a vaccine that protects against a disorder (being at least a reduction in clinical symptoms, preferably also a reduction of infection and more preferably also a reduction of the risk of mortality) arising from an infection with *Streptococcus suis* bacteria, wherein the protection is against bacteria of multiple serotypes.

To this end it has been found that one can make use of *Streptococcus suis* antigens corresponding to *Streptococcus suis* bacteria of a predetermined serotype in the manufacture of a vaccine for administration to a sow or gilt, to protect a piglet through the intake of colostrum of the said sow or gilt, against a disorder arising from *Streptococcus suis* bacteria of a serotype other than the predetermined one (next to the inherent homologous protection as known from the prior art). Applicant has shown that when the sow or gilt is vaccinated with a vaccine based on antigens of *Streptococcus suis* bacteria of a certain serotype, a piglet is protected against a disorder arising from *Streptococcus suis* bacteria of another serotype when the piglet takes in colostrum of the said sow or gilt. Given the prior art that specifically and persistently teaches that a vaccine containing antigens of *Streptococcus suis* bacteria of a predetermined serotype does not provide protection against *Streptococcus suis* bacteria of another serotype, even in case of passive immunisation through the intake of colostrum, this could not have been reasonably expected. Note that many embodiments for the use according to the present invention can be devised, once knowing that cross protection against bacteria of another serotype can be provided by immunising the sow or gilt against *Streptococcus suis* bacteria of a predetermined serotype. For example, bacteria could be put in the vaccine as such (either live attenuated or killed), the bacteria could be used to obtain an extract of one or more immunogenic components of the bacterium to put in the vaccine, or they could be used to arrive at a recombinant subunit of the bacterium to be used as the actual antigen to formulate the vaccine itself. All of these embodiments are covered by the terms "use of *Streptococcus suis* antigens in the manufacture of a vaccine".

It is noted that a vaccine in the sense of this invention is a constitution suitable for application to an animal (including humans), comprising one or more antigens such as attenuated or killed microorganisms and/or subunits thereof, or any other substance such as a metabolite of an organism, in an immunologically effective amount (i.e. capable of stimulating the immune system of the target animal sufficiently to at least reduce negative effects of a challenge of the wild-type micro-organisms), typically combined with a pharmaceutically acceptable carrier such as a liquid containing water, which upon administration to the animal induces an immune response for treating a disease or disorder, i.e. aiding in preventing, ameliorating or curing the disease or disorder. In general, a vaccine can be manufactured by using art-known methods that basically comprise admixing the antigens (or a composition containing the antigens) with a pharmaceutically acceptable carrier, e.g. a liquid carrier such as (optionally buffered) water or a solid carrier such as commonly used to obtain freeze-dried vaccines. Optionally other substances such as adjuvants, stabilisers, viscosity modifiers or other components are added depending on the intended use or required properties of the vaccine. For vaccination many forms are suitable, in particular liquid formulations (with dissolved, emulsified or suspended antigens) but also solid formulations such as implants or an intermediate form such as a solid carrier for the antigen suspended in a liquid. Parenteral and oral vaccination and suitable (physical) forms of vaccines for such vaccination have been known for more than 200 years.

In an embodiment the predetermined serotype is chosen out of the group consisting of serotype 1, 2, 7 and 9, and protection is provided against bacteria of a heterologous serotype out of the same group. *Streptococcus suis* bacteria of these serotypes are the most prevalent ones and the invention thus provides the option to formulate a vaccine containing antigens corresponding to *S. suis* bacteria of only one serotype, to obtain protection against bacteria of the four most prevalent serotypes.

In another embodiment, the predetermined serotype is chosen out of the group consisting of serotype 1 and 2, and protection is provided against bacteria of a heterologous serotype out of the group consisting of serotype 1, 2, 7 and 9. It is expected that homologous protection is still the most adequate one. Therefore, it is most advantageous to have antigens of bacteria corresponding to *S. suis* bacteria of serotype 1 and/or 2 (which are dominant in the field) in the actual vaccine. This provides a nearly perfect balance between adequate protection in the field and reduction of manufacturing risks.

In yet another embodiment, the predetermined serotype is serotype 2 and protection is provided against bacteria of a serotype out of the group consisting of serotype 1, 7 and 9. Alternatively, the predetermined serotype is serotype 1 and protection is provided against bacteria of serotype 2.

In another embodiment the vaccine comprises inactivated cells of *Streptococcus suis* bacteria and/or derivatives thereof. It appears that a vaccine comprising inactivated cells and/or derivatives thereof provides sufficient protection. The advantage of an inactive antigen is safety. The *Streptococcus suis* bacteria may be inactivated by any art-known method, such as by using chemical inactivators such as beta-propiolactone, thimerosal (or another mercury donating agent), formaldehyde etc., applying physical methods such as heat, UV-light, micro-waves etc., by using biological methods such as enzyme-based methods to kill the bacteria, and any other method as is commonly applied in the art. By using such methods, parts of the bacterial cells may lose their association with the cells. In particular, this might be the case with cell membrane associated components such as the outer membrane itself or outer membrane proteins. This way, the non-whole killed cells that remain can be regarded as derivatives in the sense of the present invention. Also, the parts that lost their association with the cells can be regarded as derivatives in the sense of the present invention. It is commonly known, in particular for outer membrane associated components, that these components can contribute in large to the effective immunological response of the target animal to the vaccine. As such, these components could be used in many cases as the sole components in the vaccine. In the latter case, one can use various art-known methods to obtain such component in (substantially) pure form, e.g. by having it made via a recombinant technique, by synthesizing the component or by purification of the component out of fermentation broth. In general, a derivative in the sense of the present invention is a non-live component of *Streptococcus suis* bacteria, other than inactivated whole cells.

In another embodiment a first vaccination of the sow or gilt is followed by a second vaccination, the first and second vaccination taking place before the sow or gilt has farrowed. This vaccination scheme has provided to lead to optimal protection of the piglet. In a preferred embodiment the first vaccination takes place 4 to 8 weeks before an expected date of farrowing and the second vaccination takes place 1 to 4 weeks before this date.

The invention also pertains to *Streptococcus suis* antigens corresponding to *Streptococcus suis* bacteria of a predetermined serotype for use in the manufacture of a vaccine for administration to a sow or gilt, to protect piglets through the intake of colostrum of the said sow or gilt, against a disorder arising from *Streptococcus suis* bacteria of a serotype other than the predetermined one.

The invention will be explained by the following examples that pertain to a preferred embodiment of the present invention.

EXPERIMENTAL DESIGN

Four sows (SPF pigs, free of clinical signs typical for *S. suis* infection) were vaccinated (intramuscular, 2 ml) with the commercially available vaccine PORCILIS STREPSUIS at 6 to 8 weeks before the expected date of farrowing and 4 weeks later (again i.m., 2 ml). This vaccine is available from Intervet Schering-Plough Animal Health, Boxmeer, the Netherlands. The vaccine comprises formaldehyde inactivated whole cells of *Streptococcus suis* serotype 2 bacteria and the active component is suspended in DILUVAC FORTE (oil-in-water) adjuvant. The vaccine contains 5% (w:w) antigen with an $OD_{600}$ of 18, which is defined as the standard or 100% vaccine strength. Likewise, other groups of four sows each were vaccinated with the following experimental vaccines: 100% vaccine containing serotypes 1, 2, 7 and 9; 50% vaccine (1, 2, 7, 9); 100% vaccine (2, 7, 9); 100% vaccine (1, 7, 9); 100% vaccine (1, 2, 9); and 100% vaccine (1, 2, 7); see Table 1.

In general, any other vaccine comprising *S. suis* antigens can be formulated by using art-known methods that basically comprise admixing suitable antigens of *S. suis* (live or inactivated, whole cell, extract, purified fraction or even subunit) with a pharmaceutically acceptable carrier, e.g. a liquid carrier such as (optionally buffered) water or a solid carrier such as commonly used to obtain freeze-dried vaccines. Optionally other substances such as adjuvants, stabilisers, viscosity modifiers or other components are added depending on the intended use or required properties of the vaccine. In the present example we used the commercially available vaccine and the experimental vaccines as mentioned here-above.

Per serotype four non-vaccinated sows were included as negative controls. At approximately 3 weeks of age, two piglets from each sow were transferred to the experimental farm. Subsequently, these piglets (in total 8 piglets per treatment group) were challenged with *S. suis* serotype 1 or 2 or 7 or 9. Group treatment (challenge groups) was performed as described in Table 1. Post mortem examination was performed at 7 days (serotypes 1, 7 and 9) or 14 days (serotype 2) after challenge or earlier in case the animal died or had to be euthanized for animal welfare reasons.

The challenge strains are field isolates (live strains) of either *S. suis* serotype 1 or 2 or 7 or 9. The challenge cultures were freshly prepared prior to challenge. *S. suis* was cultured on Todd Hewitt agar plates and incubated overnight at 37° C. Bacteria were harvested with 5 ml Todd Hewitt broth (containing 0.1% (w:v) cystein) per plate and 1 ml bacterial suspension was used to inoculate 40 ml of the same broth. Bacterial suspension was added to the broth until an $OD_{600}$ of 0.1-0.2 was reached. This was followed by incubation at 37° C. for 4-5 hours. Then, the culture was concentrated or diluted to obtain the appropriate vaccine strength (see Table 1). The challenge materials were kept on melting ice until use, which use was within 2 hours. Groups of eight piglets each were challenged with serotype 2 by the aerosol route in an aerosol box, using a Devilbis Nebulizer (40 ml of challenge culture per 16 piglets). The piglets were left in the aerosol box for approximately 30 minutes. Groups of eight piglets each were challenged with serotype 1 or 7 or 9 by intratracheal injection of 2 ml challenge culture with an appropriate OD. For treatment groups and dosage, see Table 1. Per challenge serotype a non-vaccinated control group was used.

TABLE 1

Treatment groups (vaccination sows, and challenge piglets)

| Sow group (n = 4) | Piglet group (n = 8) | Vaccine | Challenge serotype[a] |
|---|---|---|---|
| 1 | 1 | Porcilis Strepsuis | 1[b] |
| 2 | 2 | (100% serotype 2) | 7[b] |
| 3 | 3 | | 9[b] |
| 4 | 4 | 100% 1, 2, 7, 9 | 1 |
| 5 | 5 | | 2[b] |
| 6 | 6 | | 7 |
| 7 | 7 | | 9 |
| 8 | 8 | 50% 1, 2, 7, 9 | 1 |
| 9 | 9 | | 2 |
| 10 | 10 | | 7 |
| 11 | 11 | | 9 |
| 12 | 12 | 100% 2, 7, 9 | 1 |
| 13 | 13 | 100% 1, 7, 9 | 2 |
| 14 | 14 | 100% 1, 2, 9 | 7 |
| 15 | 15 | 100% 1, 2, 7 | 9 |
| 16 | 16 | — | 1 |
| 17 | 17 | — | 2 |
| 18 | 18 | — | 7 |
| 19 | 19 | — | 9 |

[a]Challenge routes: serotype 2, aerosol (40 ml/16 piglets); serotypes 1, 7 and 9, intratracheal, 2 ml per piglet
[b]OD's of challenge cultures were as follows: serotype 1, OD = 5.0; serotype 2, OD = 2.0; serotype 7, OD = 1.0; serotype 9, OD = 7.5

After challenge, rectal temperature, general condition, locomotion, nervous system and other abnormalities were scored daily.

The scoring system for the general condition was as follows:
0=normal
1=less active
2=unable to rise
4=died/moribund.

The scoring system for the locomotory system was as follows:
0=normal
1=swollen and/or painful joints
2=lame (limping on one or more legs)
3=cannot stand on one leg The scoring system for the nervous system was as follows:
0=normal behavior
1=torticollis (wryneck)
2=swinging gait
3=cannot stand/convulsions Any piglet that was euthanized was automatically given a daily score of 4 for the category of clinical sign that led to the humane endpoint decision. The total clinical score per piglet was the sum of daily clinical scores from challenge to post mortem examination. During necropsy swab samples for reisolation of the challenge organisms were taken from the brain, meninges, spleen, both elbow joints and both hock joints. The swabs were streaked out on Todd Hewitt agar plates. The plates were incubated overnight at 37° C. after which the numbers of typical *S. suis* colonies on the plates were counted. From each plate, material of typical colonies was checked for identity (*S. suis*) and serotyped with anti-*S. suis* rabbit sera. The numbers of *S. suis* colonies were converted to reisolation scores as follows:
0=no colony forming units (CFU)
1=1-10 CFU
2=11-100 CFU
3=101-1000 CFU
4=>1000 CFU Results The results of separate studies (one study per challenge serotype) are presented in tables 2-5.

TABLE 2

Results for protection of the piglets after challenge with serotype 1

| Vaccine | Mean clinical score (standard deviation) | Mortality [n/n$_{total}$] | Reisolation score (standard deviation) |
|---|---|---|---|
| Porcilis Strepsuis (100% serotype 2) | 1.6 (3.2) | 0/8 | 1.0 (1.9) |
| 100% 1, 2, 7, 9 | 2.6 (5.0) | 0/8 | 2.5 (6.0) |
| 50% 1, 2, 7, 9 | 0.1 (0.4) | 0/8 | 1.4 (1.3) |
| 100% 2, 7, 9 | 2.3 (5.3) | 1/8 | 1.4 (1.9) |
| — | 3.6 (5.9) | 1/8 | 4.3 (4.1) |

TABLE 3

Results for protection of the piglets after challenge with serotype 2

| Vaccine | Mean clinical score (standard deviation) | Mortality [n/n$_{total}$] | Reisolation score (standard deviation) |
|---|---|---|---|
| 100% 1, 2, 7, 9** | 6.4 (11.9) | 2/8 | 2.8 (4.2) |
| 50% 1, 2, 7, 9 | 23.1 (16.5) | 6/8 | 3.8 (2.5) |
| 100% 1, 7, 9 | 4.5 (10.4) | 1/8 | 0.4 (0.5) |
| — | 36.8 (16.4) | 7/8 | 5.5 (5.4) |

TABLE 4

Results for protection of the piglets after challenge with serotype 7

| Vaccine | Mean clinical score (standard deviation) | Mortality [n/n$_{total}$] | Reisolation score (standard deviation) |
|---|---|---|---|
| 100% 1, 2, 7, 9 | 13.9 (13.7) | 6/12 | 4.0 (5.7) |
| 50% 1, 2, 7, 9 | 8.7 (11.2) | 5/12 | 4.3 (5.4) |
| 100% 1, 2, 9 | 12.3 (12.7) | 6/12 | 1.8 (3.3) |
| — | 21.9 (12.4) | 8/12 | 7.3 (7.5) |

TABLE 5

Results for protection of the piglets after challenge with serotype 9

| Vaccine | Mean clinical score (standard deviation) | Mortality [n/n$_{total}$] | Reisolation score (standard deviation) |
|---|---|---|---|
| Porcilis Strepsuis (100% serotype 2) | 8.1 (7.5) | 2/8 | 2.8 (3.5) |
| 100% 1, 2, 7, 9 | 7.0 (8.7) | 2/8 | 2.0 (2.9) |
| 50% 1, 2, 7, 9 | 5.3 (5.7) | 2/8 | 2.4 (4.4) |
| 100% 1, 2, 7 | 7.3 (4.3) | 1/8 | 5.1 (3.8) |
| — | 14.1 (10.1) | 4/8 | 7.4 (9.8) |

Table 2 shows that the mean clinical score (i.e. the mean value for all 8 pigs of the total clinical score per piglet, i.e. the sum of daily clinical scores from challenge to post mortem examination) for the piglets from all vaccinated sow groups is lower than the mean clinical score for the control animals. The same is true for the reisolation score. This implies that two vaccines without serotype 1 (PORCILIS STREPSUIS only containing serotype 2 and trivalent vaccine containing serotypes 2, 7 and 9) induce (at least partial) cross-protection against serotype 1.

Table 3 shows that the mean clinical score for the piglets from all vaccinated sow groups is lower than the mean clinical score for the control animals. The same is true for the reisolation score. Results of mortality show that the 100% vaccines with serotypes 1, 2, 7 and 9 and with serotypes 1, 7 and 9 both induce a significant reduction of mortality.

This implies that the vaccine without serotype 2 (trivalent vaccine containing serotypes 1, 7 and 9) at least induced partial cross-protection against serotype 2. Combined with the results of the serotype 1 challenge study this implies that antigens of serotypes 1 and 2 give mutual cross-protection.

Table 4 shows that the mean clinical score for the piglets from all vaccinated sow groups is lower than the mean clinical score for the control animals. The same is true for the reisolation score. Results of mortality show that none of the three vaccines induce a significant reduction of mortality. The results together imply that the vaccine without serotype 7 (trivalent vaccine containing serotypes 1, 2 and 9) induced (at least partial) cross-protection against serotype 7.

Table 5 shows that the mean clinical score for the piglets from all vaccinated sow groups is lower than the mean clinical score for the control animals. The same is true for the reisolation score, although the trivalent vaccine did not induce a significant reduction of the reisolation score. Results of mortality show that the trivalent vaccine induced the largest reduction in mortality in comparison with the non-vaccinated control group. Altogether the results imply that two vaccines without serotype 9 (PORCILIS STREPSUIS only containing serotype 2 and trivalent vaccine containing serotypes 1, 7 and 9) induced (at least partial) cross-protection against serotype 9.

CONCLUSION

It has been shown that pigs can be protected against a heterologous challenge (next to a homologous challenge) when they take colostrum of a sow that has been vaccinated with antigens of *S. suis* bacteria of a specific serotype. In particular it has been shown that pigs are protected against a challenge with *S. suis* bacteria of serotype 1, 7 or 9 when they take colostrum of a sow that has been vaccinated with *S. suis* antigens of serotype 2. Given the fact that the protection has proven to be independent of the challenge serotype, which is demonstrated with a group consisting of serotypes 1, 2, 7 and 9, and also, that cross protection within the same group is provided when vaccinated with bacteria of different serotypes), it is understood that there is general cross-protection against heterologous challenge of a pig, when this pig takes colostrum of a sow vaccinated against a specific *S. suis* serotype, in particular when the vaccine contains antigens of *S. suis* bacteria belonging to a group consisting of bacteria that belong to any of the serotypes 1, 2, 7 and 9 to obtain protection against *S. suis* bacteria of a heterologous serotype from the same group.

The invention claimed is:

1. A method of protecting a piglet against a disorder arising from *Streptococcus suis* serotype 1 comprising administering to a sow or a gilt a vaccine comprising inactivated cells of *Streptococcus suis* serotype 2 wherein said protecting is achieved through the intake of colostrum by the piglet of said sow or said gilt.

2. The method of claim 1, wherein a first vaccination of the sow or the gilt is followed by a second vaccination, the first and the second vaccination taking place before the sow or the gilt has farrowed.

3. The method of claim 2, wherein the first vaccination takes place 6 to 8 weeks before an expected date of farrowing and the second vaccination takes place 2 to 4 weeks before said expected date.

4. The method of claim 1, wherein the vaccine further comprises a non-live component of the *Streptococcus suis* serotype 2.

5. The method of claim 2, wherein the vaccine further comprises a non-live component of the *Streptococcus suis* serotype 2.

6. The method of claim 3, wherein the vaccine further comprises a non-live component of the *Streptococcus suis* serotype 2.

* * * * *